United States Patent [19]

Scrivo

[11] Patent Number: 4,579,419
[45] Date of Patent: Apr. 1, 1986

[54] FIBER OPTIC CONNECTOR AND APPARATUS AND METHOD EMPLOYING SAME

[75] Inventor: Leonard Scrivo, Tuckahoe, N.Y.

[73] Assignee: Vicon Fiber Optics Corp., Pelham Manor, N.Y.

[21] Appl. No.: 537,277

[22] Filed: Sep. 29, 1983

[51] Int. Cl.⁴ ............................................... G02B 5/16
[52] U.S. Cl. .............................. 350/96.20; 350/96.24; 362/32; 433/31
[58] Field of Search ............. 350/96.20, 96.21, 96.22, 350/96.24, 96.25; 362/32; 433/31

[56] References Cited

U.S. PATENT DOCUMENTS

| | | | |
|---|---|---|---|
| 2,825,260 | 3/1958 | O'Brien | 350/96.25 |
| 2,992,587 | 7/1961 | Hicks, Jr. et al. | 350/96.25 |
| 3,131,690 | 5/1964 | Innis et al. | 362/32 X |
| 3,455,625 | 7/1969 | Brumley et al. | 350/96.22 |
| 3,578,973 | 5/1971 | Dooley et al. | 250/462.1 |
| 3,585,705 | 6/1971 | Allan | 29/412 |
| 3,638,013 | 1/1972 | Keller | 433/31 |
| 3,758,951 | 9/1973 | Scrivo et al. | 433/31 X |
| 3,837,727 | 9/1974 | Norton | 350/96.25 |
| 3,854,792 | 12/1974 | Koelle | 350/96.24 |
| 3,889,662 | 6/1975 | Mitsui | 128/6 |
| 3,958,114 | 5/1976 | Codrino | 362/32 |
| 4,025,776 | 5/1977 | Cawood et al. | 362/32 |
| 4,039,250 | 8/1977 | Gaertner | 350/96.15 |
| 4,076,378 | 2/1978 | Cole | 350/96.24 |
| 4,185,888 | 1/1980 | Quelle, Jr. | 350/96.25 |
| 4,332,439 | 6/1982 | Lübbers et al. | 350/320 |

FOREIGN PATENT DOCUMENTS 0018264 10/1980 European Pat. Off. ......... 350/96.24
82/337 10/1982 PCT Int'l Appl. .

Primary Examiner—John Lee
Attorney, Agent, or Firm—Lerner, David, Littenberg, Krumholz & Mentlik

[57] ABSTRACT

A fiber optic connector employs a fiber optic element including a light-receiving end having a transverse cross-sectional shape which complements the transverse cross-sectional shape of a light-receiving end of at least one other fiber optic element. The complementarily shaped light-receiving ends permit a plurality of fiber optic connectors to be arranged alongside one another so that they may be directly and simultaneously illuminated by a single spot of light emitted from a source of light.

13 Claims, 4 Drawing Figures

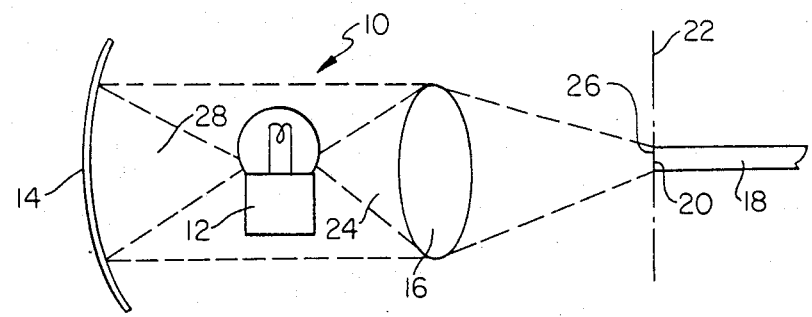
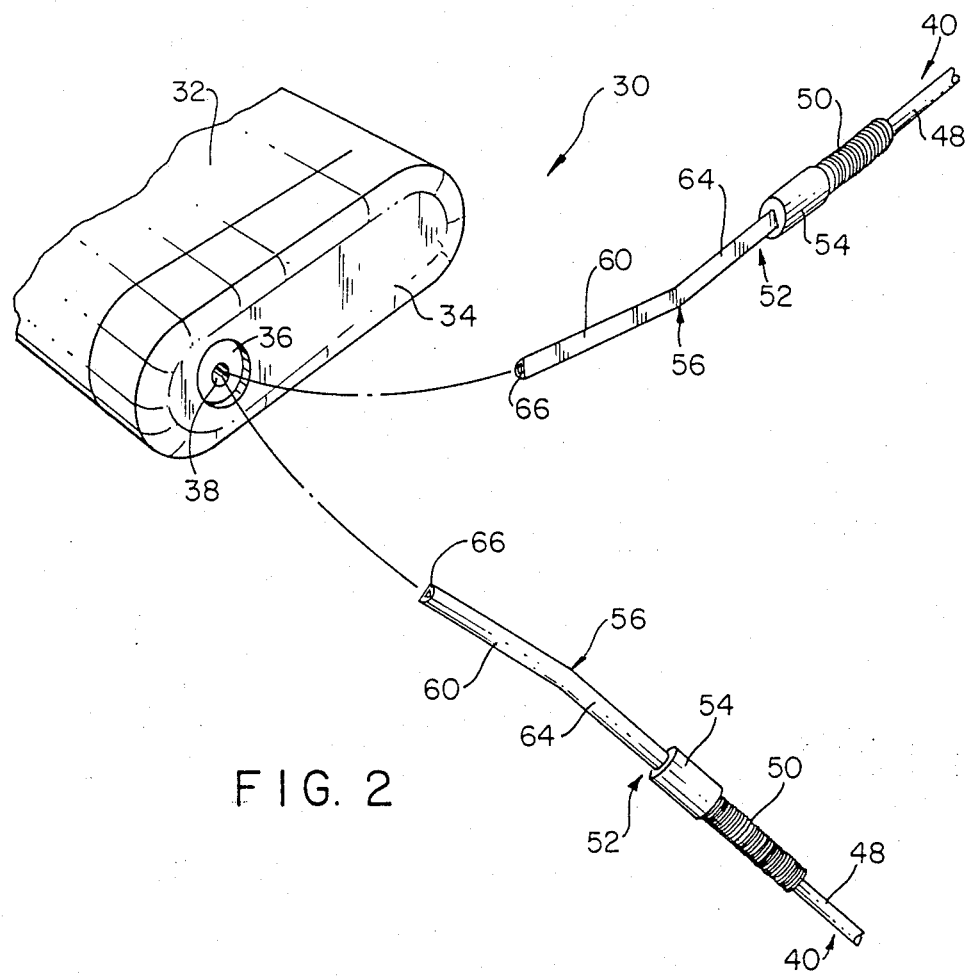

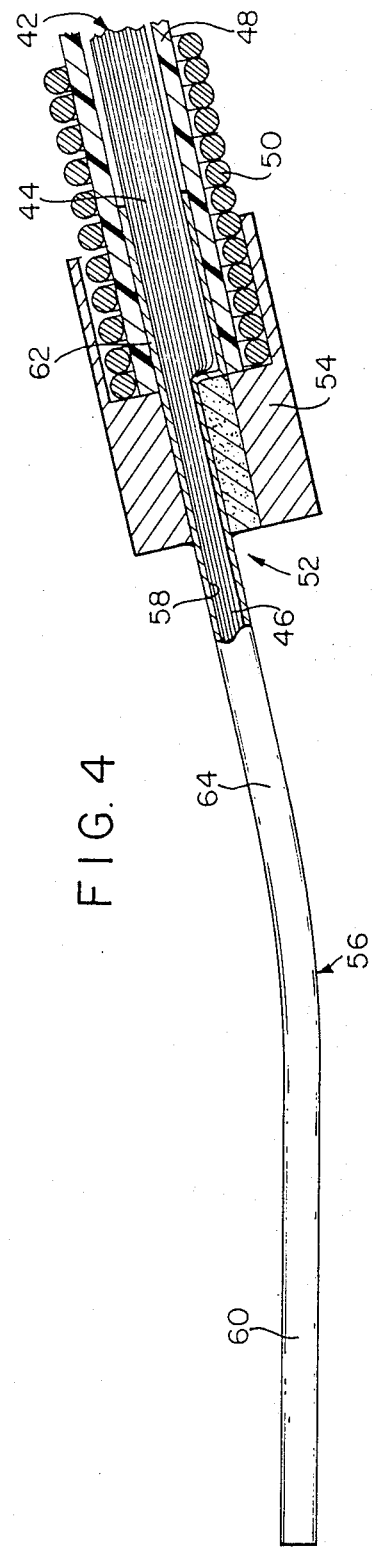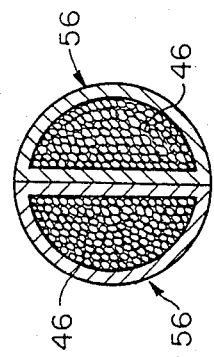

FIBER OPTIC CONNECTOR AND APPARATUS AND METHOD EMPLOYING SAME

FIELD OF THE INVENTION

The present invention relates to fiber optic illumination systems, and, more particularly, to such systems which are useful in industry as well as in the medical and dental fields.

BACKGROUND OF THE INVENTION

For many years, fiber optic illumination systems have used fiber optic bundles to transmit light to industrial, dental and medical instruments. One end of the fiber optic bundle is conventionally inserted into an opening in a receptacle which is aligned with a light source. The light is transmitted through the fiber optic bundle to the instrument at the other end of the bundle.

In certain instances, it may be desirable to light two or more instruments at the same time. U.S. Pat. No. 3,638,013, for example, describes a fiber optic illumination system which is provided with a rotatable plug having three bundle-receiving openings. The plug may be rotated so that one, two or all three of the openings are positioned to be illuminated by a light source, whereby a corresponding number of instruments can be lit.

Various fiber optic illumination systems have been proposed in the past. Typically, these systems employ a lighting unit equipped with a light bulb, a concaved reflector and a fan for dissipating the heat generated by the bulb. Due to the large size of such a unit, it is usually located relatively far away from the work area. The remote positioning of the unit necessitates the use of relatively long fiber optic bundles (i.e., bundles as long as two to three meters). Due to the light losses inherent in fiber optic bundles, which losses can be as high as fifty percent per meter, the light bulb used must emit light of a high intensity, and, therefore, it must have a relatively high wattage (i.e., in the neighborhood of one hundred and fifty watts). One disadvantage of using high wattage bulbs is that they have a relatively short operating life. Another disadvantage is that the high emission of heat will inconvenience the operator as well as the patient. Furthermore, a relatively large fan must be used to cool the unit, the size of the fan creating an undesired increase in the overall size of the unit as well as producing disturbing noise.

In European patent application Serial No. PCT/SE82/00337, filed Oct. 18, 1982, there is disclosed a relatively compact fiber optic illumination system which includes a combination lens and reflector condensing system designed to concentrate light emitted from a relatively low wattage light bulb on a light-receiving end of a fiber optic bundle. Because its light is concentrated, the low wattage bulb can illuminate the light-receiving end of the fiber optic bundle to the same extent as a higher wattage light bulb. The use of a low wattage bulb is advantageous in that it takes up less room and generates less heat than a high wattage light bulb. However, in order to illuminate more than one fiber optic bundle and therefore more than one instrument, the lens of the condensing system is adapted so as to be switchable between two or more fiber optic bundles, whereby each fiber optic bundle may be selectively and independently coupled to the light bulb. Although the switch permits a plurality of fiber optic bundles to be illuminated, they can not be illuminated simultaneously. Also, the provision of such a light switch is disadvantageous because it requires a manual switching operation.

SUMMARY OF THE INVENTION

The problems and disadvantages of the prior art devices discussed above are overcome by forming a fiber optic connector from a fiber optic element which has a light-receiving end having a transverse cross-sectional shape which complements the shape of a light-receiving end of at least one other fiber optic element, whereby a plurality of complementarily shaped light-receiving ends can be arranged alongside one another so that they may be directly and simultaneously illuminated by a single spot of light emitted from a light source, such as a low wattage light bulb. In one embodiment, the transverse cross-sectional shape of the light-receiving end is different from the transverse cross-sectional shape of the remainder of the fiber optic element. In another embodiment, the light-receiving end includes an upstream portion which terminates at one end in a light-receiving face and a downstream portion which is positioned between an opposite end of the upstream portion and the remainder of the fiber optic element. The downstream portion can be arranged at an angle relative to the upstream portion, the angle being selected such that the downstream portion diverges from a downstream portion of a complementarily shaped light-receiving end of another connector.

The new and improved connector is especially useful in connection with compact fiber optic illumination systems which normally include a housing, a light source positioned within the housing, an optical condensing system adapted to condense light emitted from the light source into a single spot of light and an opening in the housing adapted to receive a single fiber optic connector. By replacing the single fiber optic connector with two or more complementarily shaped fiber optic connectors constructed in accordance with the present invention, the single spot of light may directly and simultaneously illuminate all of the fiber optic connectors and hence a corresponding number of instruments, such as dental or medical instruments.

BRIEF DESCRIPTION OF THE DRAWINGS

For a more complete understanding of the present invention, reference is made to the following detailed description of an exemplary embodiment considered in conjunction with the accompanying drawings, in which:

FIG. 1 is a schematic illustration of a basic fiber optic illumination system;

FIG. 2 is an exploded view of a fiber optic illumination system constructed in accordance with the present invention;

FIG. 3 is a transverse cross-sectional view showing two fiber optic connectors employed by the fiber optic illumination system shown in FIG. 2, the fiber optic connectors being arranged in abutting side-by-side relationship; and FIG. 4 is a partial longitudinal cross-sectional view of one of the fiber optic connectors illustrated in FIGS. 2 and 3.

DETAILED DESCRIPTION OF THE EXEMPLARY EMBODIMENT

With reference to FIG. 1, a basic compact fiber optic illumination system 10 includes a halogen bulb 12, a concaved mirrored reflector 14 positioned behind the bulb 12, a condensing lens 16 positioned in front of the bulb 12 and a fiber optic bundle 18 whose light-receiving face 20 is positioned in a focal plane 22 of the lens 16. The reflector 14 and the lens 16 cooperate to form an optical condensing system which operates in the following manner. One cone 24 of light emitted from the bulb 12 is focused by the lens 16 onto a spot 26 lying in the focal plane 22 of the lens 16. The spot 26 of light has a diameter which is substantially equal to the diameter of the light-receiving face 20 of the fiber optic bundle 18 (i.e., about 3 millimeters) so that substantially all of the condensed light can be focused directly on the light-receiving face 20 of the fiber optic bundle 18. Another cone 28 of the light emitted from the bulb 12 is reflected off of the reflector 14 and focused by the lens 16 on the spot 26. All of the condensed light which is focused on the light-receiving face 20 of the fiber optic bundle 18 is then transmitted through the fiber optic bundle 18 to an instrument, such as a dental drill (not shown).

Referring to FIGS. 2-4, a compact fiber optic illumination system 30 constructed in accordance with the present invention includes a housing 32 which is provided at one end 34 with a fiber optic receptacle 36 having an opening 38 sized and shaped so as to receive two identical fiber optic light carriers 40 such that they directly and simultaneously receive light which is focused or condensed in the manner described above with reference to FIG. 1. Each fiber optic light carrier 40 includes a fiber optic bundle 42 having a body 44 provided with a generally circular transverse cross-sectional shape and a light-receiving end 46 which has a semi-circular transverse cross-sectional shape (see FIGS. 3 and 4). The body 44 of the fiber optic bundle 42 is encased in a piece of flexible tubing 48. Each fiber optic light carrier 40 also includes a conventional strain relief spring 50 and a fiber optic connector assembly 52. Because the strain relief spring 50 and the flexible tubing 48 are of conventional design and construction, there is no need to describe these elements in greater detail.

Each of the fiber optic connector assemblies 52, which assemblies form the heart of the present invention, includes a stainless steel ferrule 54 and a stainless steel termination tube 56 soldered or otherwise attached to the ferrule 54. The termination tube 56 is provided with a longitudinal channel 58 having a semi-circular transverse cross-sectional shape which substantially matches the semi-circular transverse cross-sectional shape of the light-receiving end 46 of the fiber optic bundle 42. The termination tube 56 also includes an upstream portion 60, a socket 62 and a downstream portion 64 positioned between the upstream portion 60 and the socket 62. The downstream portion 64 is arranged at an angle relative to the upstream portion 60 to give the termination tube 56 an angular configuration. Because of the flexibility of the fiber optic bundle 42, the light-receiving end 46 of the fiber optic bundle 42 conforms to the angular configuration of the termination tube 56.

The upstream portion 60 and the downstream portion 64 of each of the termination tubes 56 have a semi-circular transverse cross-sectional shape. More particularly, the semi-circular transverse cross-sectional shapes of the two termination tubes 56 are complementary so that both of the termination tubes 56 can be inserted into the opening 38 in the fiber optic receptacle 36 in abutting side-by-side relationship (see FIG. 3). The socket 62 of each of the termination tubes 56 has a circular transverse cross-sectional shape so that it can receive the body 44 of a corresponding one of the fiber optic bundles 42.

When the termination tubes 56 are inserted into the opening 38 of the fiber optic receptacle 36 in abutting side-by-side relationship, their upstream portions 60 are arranged parallel to each other, while their downstream portions 64 diverge from each other to facilitate insertion of the fiber optic light carriers 40 into the opening 38 and to inhibit the fiber optic light carriers 40 from interfering with one another during and after insertion. The length of each of the upstream portions 60 is selected such that light-receiving faces 66 (see FIG. 2) of the fiber optic bundles 42 are automatically positioned in the housing 32 so as to receive a spot of concentrated light.

If, on one hand, the fiber optic light carriers 40 are supplied as original equipment, the light-receiving face 66 of each of the fiber optic bundles 42 can be provided with a surface area equal to the surface area of a light-receiving face of a fiber optic bundle employed by a conventional fiber optic connector assembly having a standard circular transverse cross-sectional shape, whereby the amount of light transmitted through each of the new and improved fiber optic light carriers 40 is substantially the same as the amount of light transmitted through the conventional fiber optic light carriers. If, on the other hand, the existing fiber optic illumination systems are retrofitted with the new and improved fiber optic light carriers 40, the light-receiving face 66 of each of the fiber optic bundles 42 would have a surface area which is approximately one half the surface area of the light-receiving faces of the conventional fiber optic light carriers. Although less light would be transmitted through each of the fiber optic bundles 42 because of the reduced surface area of the light-receiving faces 66, the reduction would not have a deleterious affect on the operation of the fiber illumination system 30. If it is desirable to avoid any such reduction in the transmission of light through the fiber optic bundles 42, the standard fiber optic receptacle can be replaced with a new one having a larger opening adapted to receive two of the new and improved fiber optic light carriers 40, the light-receiving faces 66 of which would have the same surface area as the light-receiving faces of the fiber optic bundles employed by the conventional fiber optic light carriers employing connectors with circular transverse cross-sectional shapes.

It will be understood that the embodiment described herein is merely exemplary and that a person skilled in the art may make many variations and modifications without departing from the spirit and scope of the invention. For instance, more than two complementarily shaped fiber optic connectors can be employed simultaneously. Also, the light-receiving ends of the fiber optic connectors can have any desired transverse cross-sectional shape, such as triangular, rectangular and square. All such modifications and variations are intended to be included within the scope of the invention as defined in the appended claims. I claim:

1. A compact fiber optic illumination system, comprising a housing, a light source positioned within said housing, condensing means positioned within said housing for condensing light emitted from said light source into a single spot of light lying in a plane within said housing, an opening in said housing and a plurality of complementarily shaped fiber optic connectors removably received in said opening in said housing such that said fiber optic connectors may be directly and simultaneously illuminated by said single spot of light, each of said fiber optic connectors including a fiber optic element having a light-receiving end provided with a transverse cross-sectional shape which is different from the transverse cross-sectional shape of the remainder of said fiber optic element, said transverse cross-sectional shape of said light-receiving end complementing the transverse cross-sectional shape of said light-receiving end of each of said other fiber optic elements.

2. A compact fiber optic illumination system according to claim 1, wherein said light-receiving end of each of said fiber optic elements has a light-receiving face.

3. A compact fiber optic illumination system according to claim 2, wherein said light-receiving end of each of said fiber optic elements includes an upstream portion which terminates at one end in said light-receiving face and a downstream portion which is positioned between an opposite end of said upstream portion and said remainder of said fiber optic element, said downstream portion being arranged at an angle relative to said upstream portion.

4. A compact fiber optic illumination system according to claim 3, wherein said angle of said downstream portion of each fiber optic element is selected such that said downstream portion diverges from a downstream portion of each of the other fiber optic elements.

5. A compact fiber optic illumination system according to claim 4, wherein said light-receiving end of each of said fiber optic elements is housed in a hollow open-ended casing having a longitudinal channel extending therethrough, said channel having a transverse cross-sectional shape which substantially matches said transverse cross-sectional shape of said corresponding light-receiving end.

6. A compact fiber optic illumination system according to claim 5, wherein said casing is made of metal.

7. A compact fiber optic illumination system according to claim 6, wherein said upstream portion of each of said fiber optic elements has a length selected such that said light-receiving faces are automatically positioned in said plane within said housing when said fiber optic connectors are received in said opening in said housing.

8. A compact fiber optic illumination system according to claim 1, wherein said transverse cross-sectional shape of said light-receiving end of each of said fiber optic elements is a sector of a circle.

9. A compact fiber optic illumination system according to claim 8, wherein said transverse cross-sectional shape of said light-receiving end of each of said fiber optic elements is semi-circular.

10. A compact fiber optic illumination system according to claim 9, wherein said transverse cross-sectional shape of said remainder of each of said fiber optic elements is circular.

11. A compact fiber optic illumination system according to claim 9, wherein said opening in said housing has a circular shape which substantially matches the circular shape formed by said semi-circular shaped light-receiving ends of said fiber optic elements.

12. A method of retrofitting a fiber optic illumination system which normally includes a housing, a light source positioned within said housing, condensing means positioned within said housing for condensing light emitted from said light source into a single spot of light lying in a plane within said housing, an opening in said housing and a single fiber optic connector removably received in said opening in said housing, said method comprising the step of replacing said single fiber optic connector with a plurality of complementarily shaped fiber optic connectors, each of said complementarily shaped fiber optic connectors being removably received in said opening in said housing such that said single spot of light directly and simultaneously illuminates said plurality of fiber optic connectors, each of said fiber optic connectors including a fiber optic element having a light-receiving end provided with a transverse cross-sectional shape which is different from the tranverse cross-sectional shape of the remainder of said fiber optic element, said transverse cross-sectional shape of said light-receiving end complementing the transverse cross-sectional shape of said light-receiving end of each of said other fiber optic elements.

13. A method of illuminating a plurality of instruments using a compact fiber optic illumination system which includes a housing, a light source positioned within said housing, condensing means positioned within said housing for condensing light emitted from said light source into a single spot of light lying in a plane within said housing, and an opening within said housing, said method comprising the step of inserting a plurality of complementarily shaped fiber optic connectors into said opening in said housing such that all of said fiber optic connectors are directly and simultaneously illuminated by said single spot of light, each of said fiber optic connectors including a fiber optic element having a light-receiving end provided with a transverse cross-sectional shape which is different from the tranverse cross-sectional shape of the remainder of said fiber optic element, said transverse cross-sectional shape of said light-receiving end complementing the transverse cross-sectional shape of said light-receiving end of each of said other fiber optic elements, whereby a plurality of instruments may be lit from light emitted from a relatively low wattage bulb functioning as said light source.

* * * * *